(12) United States Patent
Bindl et al.

(10) Patent No.: US 9,126,897 B2
(45) Date of Patent: Sep. 8, 2015

(54) SYNTHESIS OF DIAMIDO GELLANTS BY USING AMINO ACID N-CARBOXYANHYDRIDES

(71) Applicant: EVONIK INDUSTRIES AG, Essen (DE)

(72) Inventors: Martin Bindl, Ludwigshafen (DE); Roland Herrmann, Maintal (DE); Gunter Knaup, Bruchkobel (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/402,847

(22) PCT Filed: May 13, 2013

(86) PCT No.: PCT/EP2013/059760
§ 371 (c)(1),
(2) Date: Nov. 21, 2014

(87) PCT Pub. No.: WO2013/178451
PCT Pub. Date: Dec. 5, 2013

(65) Prior Publication Data
US 2015/0175527 A1  Jun. 25, 2015

Related U.S. Application Data

(60) Provisional application No. 61/654,747, filed on Jun. 1, 2012.

(51) Int. Cl.
*C07C 231/02* (2006.01)

(52) U.S. Cl.
CPC .................................... *C07C 231/02* (2013.01)

(58) Field of Classification Search
CPC ....................................................... C07C 231/02
See application file for complete search history.

(56) References Cited

PUBLICATIONS

Wagler et al., "Synthesis of a Chiral Dioxo-Cyclam Derived from L-Phenylalanine and its Application to Olefin Oxidation Chemistry", Tetrahedron Letters, vol. 29, No. 40, pp. 5091-5094, 1988.

*Primary Examiner* — Shailendra Kumar
(74) *Attorney, Agent, or Firm* — Reed Smith LLP; Eric J. Evain; Maryellen Feehery Hank

(57) ABSTRACT

The invention relates to a method for the synthesis of a compound according to formula I comprising the following steps: a) reacting a N-carboxyanhydride according to formula II and a N-carboxy-anhydride according to formula III with a diamine according to formula IV and b) adding an acid to the reaction to adjust the pH value of the reaction to <7; wherein L represents a $C_2$-$C_{20}$ alkyl group, a $C_6$-$C_{20}$ aryl group, or a $C_7$-$C_{20}$ alkylaryl group; and $R^1$ and $R^2$ can be identical or different and represent a hydrogen atom, a $C_1$-$C_4$ alkyl group, a $C_1$-$C_4$ hydroxyalkyl group, a $C_1$-$C_4$ thioether group, a $C_6$-$C_{20}$ aryl group, a $C_7$-$C_{20}$ alkylaryl group, a $C_7$-$C_{20}$ alkylhydroxyaryl group, a $C_4$-$C_{20}$ alkylheteroaryl group with 1 to 4 heteroatoms; or a $C_1$-$C_4$ alkylcarboxylic moiety, which may be an acid, an amide, or which may be esterified with a $C_1$-$C_6$ alkyl group or a $C_7$-$C_{20}$ alkylaryl group.

20 Claims, No Drawings

SYNTHESIS OF DIAMIDO GELLANTS BY USING AMINO ACID N-CARBOXYANHYDRIDES

RELATED APPLICATIONS

This application is a national stage application (under 35 U.S.C. §371) of PCT/EP2013/059760, filed May 13, 2013, which claims benefit of U.S. application 61/654,747, filed Jun. 1, 2012. Application PCT/EP2013/059760 claims the benefit of U.S. Provisional Application 61/654,747 filed on Jun. 1, 2012. The entire contents of each application are hereby incorporated by reference.

The present invention relates to a method for the synthesis of diamido gellants from diamines and amino acid N-carboxyanhydrides.

Diamido compounds of the general formula

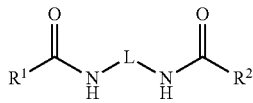

wherein $R^1$ and $R^2$ are amino-functional end-groups and L is a linking moiety of molecular weight from 14 to 500 g/mol are known in the art to serve as gellants to thicken liquid compositions. Such gellants have, for example, been described in WO 2011/112912 A1 and WO 2011/112887 A1.

Gellants are used to provide structure and a pleasant texture to liquid consumer products such as, for example, liquid detergent compositions. Furthermore, gellants can stabilize other components within the product such as, for example, enzymes and bleaches. However, gellants need to be selected carefully to prevent incompatibilities between the gellant and other components of the composition and unwanted side effects such as clouding of the liquid composition.

Diamido gellants offer the significant advantage over other gellants of being compatible with a broad range of consumer products and not affecting product clarity.

A synthesis of diamido gellants is described in WO 2011/112887 A1. In this synthesis, N-benzyloxycarbonyl-L-valine is coupled to diaminopropane using N,N'-Dicyclohexylcarbodiimide as coupling reagent. The currently known synthesis of diamido gellants therefore requires the use of N-benzyloxycarbonyl or N-(tert-butyloxycarbonyl) protected amino acids. However, such a synthesis method is expensive, mainly due to the cost of the protected amino acids, and requires additional steps to remove the protecting groups.

Hence, there is the need for a cheaper and faster strategy for the synthesis of diamido gellants.

To this end, the present invention provides a method for the synthesis of a compound according to formula I

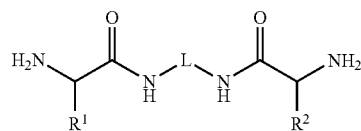

comprising the following steps:
a) reacting a N-carboxyanhydride according to formula II

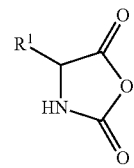

and a N-carboxyanhydride according to formula III

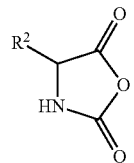

with a diamine according to formula IV

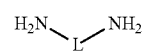

and
b) adding an acid to the reaction to adjust the pH value of the reaction to <7; wherein L represents a $C_2$-$C_{20}$ alkyl group, a $C_6$-$C_{20}$ aryl group, or a $C_7$-$C_{20}$ alkylaryl group; and $R^1$ and $R^2$ can be identical or different and represent a hydrogen atom, a $C_1$-$C_6$ alkyl group, a $C_1$-$C_4$ hydroxyalkyl group, a $C_1$-$C_4$ thioether group, a $C_6$-$C_{20}$ aryl group, a $C_7$-$C_{20}$ alkylaryl group, a $C_7$-$C_{20}$ alkylhydroxyaryl group, a $C_4$-$C_{20}$ alkylheteroaryl group with 1 to 4 heteroatoms;

or a $C_1$-$C_4$ alkylcarboxylic moiety, which may be an acid, an amide, or which may be esterified with a $C_1$-$C_4$ alkyl group or a $C_7$-$C_{20}$ alkylaryl group.

An alkyl group is a linear, branched, or cyclic hydrocarbon chain. It may also be a combination of linear, branched, and cyclic structures. A $C_n$-$C_m$ alkyl is a hydrocarbon having n to m carbon atoms.

An aryl group is an aromatic hydrocarbon. The aryl may be monocyclic or polycyclic. In the case of polycyclic aryls, the individual aromatic rings may be fused or may be connected by single carbon-carbon bonds. Examples for suitable aryl groups are phenyl, biphenyl, naphtyl, anthryl, or phenanthryl. A $C_n$-$C_m$ aryl is an aromatic hydrocarbon having n to m carbon atoms.

A heteroaryl group is an aromatic hydrocarbon that contains 1 to 4 heteroatoms, preferably 1 to 2 heteroatoms. The heteroatoms may be oxygen, sulfur, and/or nitrogen. The heteroaryl may be monocyclic or polycyclic. The heteroaryl group may be attached to the main molecule through any of its carbon or nitrogen atoms.

An alkylaryl group is an aryl group that is substituted with one or more alkyl groups. The alkylaryl group may be attached to the main molecule through any of its alkyl or aryl carbon atoms. A $C_n$-$C_m$ alkylaryl contains n to m carbon atoms.

An alkylheteroaryl group is a heteroaryl group that is substituted with one or more alkyl groups. The alkyl substituents may be attached to the heteroaryl through any of the aromatic carbon or nitrogen atoms. The alkylheteroaryl group may be attached to the main molecule through any of the alkyl carbon atoms and/or the heteroaryl carbon or nitrogen atoms.

A hydroxyalkyl group is an alkyl group that is substituted with one or more hydroxyl groups. A $C_n$-$C_m$ hydroxyalkyl group contains n to m carbon atoms.

A thioether group refers to two alkyl groups that linked by a thioether bond. A $C_n$-$C_m$ thioether group contains n to m carbon atoms in total. The thioether group may be attached to the main molecule through any of its carbon atoms.

An alkylhydroxyaryl group is an alkylaryl group, in which any of the aryl carbon atoms are substituted with a hydroxyl group. The alkylhydroxyaryl group may be attached to the main molecule through any of its alkyl or aryl carbon atoms. A $C_n$-$C_m$ alkylhydroxyaryl contains n to m carbon atoms.

A $C_1$-$C_4$ alkylcarboxylic moiety, which may be an acid, an amide, or which may be esterified with a $C_1$-$C_6$ alkyl group or a $C_7$-$C_{20}$ alkylaryl group. In case of an amide, the nitrogen of the amide functionality is substituted with two hydrogen atoms. The alkyl ester group is a linear, branched, or cyclic hydrocarbon chain. It may also be a combination of linear, branched, and cyclic structures. An alkylaryl group is an aryl group that is substituted with one or more alkyl groups. The alkylaryl group may be attached to the carboxylic fragment through any of its alkyl or aryl carbon atoms. A $C_1$-$C_4$ alkylcarboxy group contains 1 to 4 carbon atoms in total.

In the investigations leading to the present invention it has been surprisingly found that amino acid N-carboxyanhydrides according to formulae II and III selectively react with diamino compounds to form amide bonds between the amino groups of the diamino compound and the $C_\alpha$ atom of the amino acid, without unwanted polymerization of the N-carboxyanhydrides. By using amino acid N-carboxyanhydrides according to formulae II and III, the present invention circumvents the need for N-benzyloxycarbonyl or N-(tert-butyloxycarbonyl) protected amino acids. Furthermore, the carbamic acid moiety, which remains after the N-carboxyanhydride is coupled to the amino group, is readily cleaved under acid conditions to deprotect the α-amino group. Therefore, no additional steps to remove any protection groups are required.

N-carboxyanhydrides according to formulae II and III are easily accessible through the direct reaction of free α-amino acids with phosgene. As a further advantage of the present invention, this reaction can be performed in situ prior to step a), without the need for isolating the N-carboxyanhydrides.

Preferably $R^1$ and $R^2$ independently represent a hydrogen atom, a n-butyl group, a t-butyl group, a propyl group, a cyclopropyl group, an ethyl group, or one of the side chains of the amino acids alanine, valine, leucine, isoleucine, methionine, phenylalanine, tyrosine, tryptophan, serine, threonine, glutamine, asparagine, esters of glutamic acid, or esters of aspartic acid. Here, the expression "side chain" refers to the substituent group attached to the $C_\alpha$ atom of an α-amino acid. Esters of glutamic or aspartic acid are esterified with a $C_1$-$C_6$ alkyl or a $C_7$-$C_{20}$ alkylaryl group on the side chain carboxylic acid moiety. Preferably, esters of glutamic or aspartic acid are esterified with an ethyl group on the side chain carboxylic acid moiety. For the above-mentioned amino acids, the side chains are methyl, isopropyl, isobutyl, sec-butyl, 2-thiomethyl-ethyl, benzyl, 4-hydroxybenzyl, 3-methylindol, hydroxymethyl, 1-hydroxyethyl, carboxamidoethyl, carboxamidomethyl, alkoxycarbonylethyl, alkoxycarbonylmethyl, arylalkoxycarbonylethyl or arylalkoxycarbonylmethyl.

In a particularly preferred embodiment, $R^1$ and $R^2$ independently represent a $C_1$ to $C_4$ unsubstituted alkyl group. In another particularly preferred embodiment, $R^1$ and $R^2$ independently represent one of the side chains of the amino acids alanine, valine, leucine, isoleucine, or phenylalanine.

$R^1$ and $R^2$ can be identical or different. If $R^1$ and $R^2$ are identical, the N-carboxyanhydrides according to formulae II and III are identical, i.e. a single N-carboxyanhydride is used to synthesize the diamido compound according to formula I. The resulting diamido compound is symmetrically substituted. If on the other hand $R^1$ and $R^2$ are different, the resulting diamido compound according to formula I is a mixture of differently substituted diamido compounds.

Preferred diamino compounds according to formula IV are those, wherein L represents a $C_6$-$C_{12}$ linear alkyl group, a 1,4-dimethylcyclohexyl group, or a xylene group. In a particularly preferred embodiment, the diamino compound according to formula IV is selected from the following list.

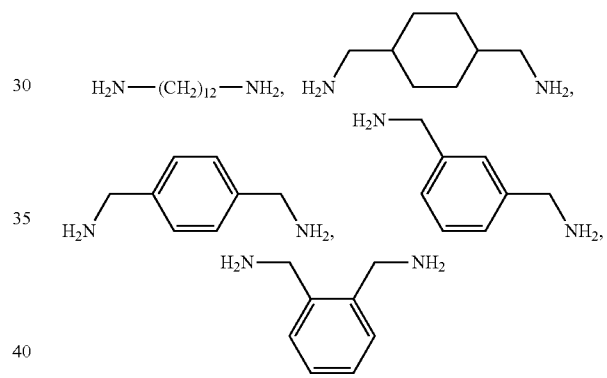

To prevent polymerization of the N-carboxyanhydrides and to ensure quantitative amidation of the diamino compound, the N-carboxyanhydrides according to formulae II and III are preferably provided in an initial total molar amount that is 2 to 3.5-fold higher than the initial molar amount of the diamine. More preferably the initial molar excess of the total amount of N-carboxyanhydrides over the diamino compound is 2.5 to 3.1-fold.

Preferably the reaction between the N-carboxyanhydrides according to formulae II and III and the diamino compound according to formula IV is carried out in a polar aprotic solvent. Suitable solvents for the present invention are, for example, dichloromethane, methyl tert-butyl ether, tetrahydrofuran, ethyl acetate, dimethylformamide, acetonitrile, dimethylsulfoxide, methyl isobutyl ketone, methyl ethyl ketone, acetone or mixtures thereof.

The reaction between the N-carboxyanhydrides according to formulae II and III and the diamino compound according to formula IV may be improved by addition of a base. Preferably, a non-nucleophilic base is added to the reaction mixture of step a). Suitable compounds for this purpose are, for example, triethylamine, diisopropylethylamine, or mixtures thereof.

The reaction between the N-carboxyanhydrides according to formulae II and III and the diamino compound according to formula IV is carried out in solution and is started by mixing the two reactants. In a preferred embodiment of the present invention, N-carboxyanhydrides according to formulae II and III and the diamino compound according to formula IV are each provided as separate solutions at a temperature of −10 to +30° C., more preferably of 0 to 15° C. The solution of the diamino compound is then added to the solution of the N-carboxyanhydride to start the reaction. If a base is used to improve the reaction, the base is added after addition of the diamino compound.

The reaction mixture is stirred until the diamino compound has completely reacted with the N-carboxyanhydrides. Preferably, the reaction time is up to 12 hours, more preferably 1 to 3 hours. The reaction temperature is adjusted according to the melting and the boiling point of the solvent and the thermal stability of the reagents. Preferably, the reaction is carried out at a temperature of 0 to 30° C., more preferably at 5 to 15° C.

After the coupling of the N-carboxyanhydride to the diamino compound in step a) the reaction mixture is acidified by addition of an acid and water. Acidification results in hydrolysis of the carbamic acid moiety and release of the diamido product according to formula I. Preferably the pH of the reaction mixture is adjusted to a value, which ensures complete hydrolysis of the carbamic acid moiety, more preferably to a pH of 1 to 2. Preferably, the acid is an aqueous solution of hydrochloric acid.

The diamido product according to formula I is preferably isolated from the reaction mixture after step b). This can be achieved by extraction of the acidic, aqueous phase with a water immiscible, organic solvent and subsequently adjustment to a basic pH, preferably a pH above 10 and extraction of the diamido product by a water immiscible, organic solvent. The diamido product can be further purified by crystallization from the organic phase.

In a preferred embodiment of the invention, the reaction in step a) is carried out in a polar aprotic solvent at a temperature of 5 to 15° C., and in the presence of a non-nucleophilic base. In this embodiment, the initial molar excess of the total amount of N-carboxyanhydrides over the diamino compound is 2.5 to 3.1-fold and in step b) the pH is adjusted to 1 to 2.

EXAMPLES

Example 1

Synthesis of L-valine-N-carboxyanhydride

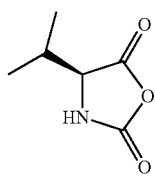

A 4-necked 2 L flask is equipped with a mechanical stirrer and a condenser, which is charged with dry ice. L-valine (117.2 g, 1.0 mol) is suspended in THF (1 L) and phosgene (150 g, 1.5 mol) is added during 30 min. The temperature rises to 50° C. The reaction mixture is stirred under reflux (approx. 60° C.) until a clear solution is obtained (after approx. 40 min). Nitrogen was purged through the solution during 1 h to remove excess of phosgene. The solvent is evaporated and the residue is dissolved in toluene (1 L). Heptane (0.6 L) is added and the suspension is stirred at 0° C. for 1 h. The precipitate is filtered off, washed twice with toluene/heptane (1:2, 0.15 L) and dried at 60° C. in vacuum. Yield: 115.9 g (81%).

$^1$H-NMR (600 MHz, DMSO): δ=9.09 (s, 1H), 4.35 (d, J=3 Hz, 1H), 2.08-2.03 (m, 1H), 0.96 (d, J=6 Hz, 3H), 0.87 (d, J=6 Hz, 3H) ppm.

Example 2

Synthesis of L-phenylalanine-N-carboxyanhydride

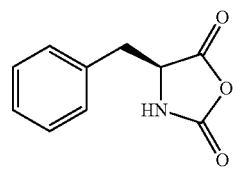 [SMILES: O=C1N[C@@H](Cc2ccccc2)C(=O)O1]

L-phenylalanine-N-carboxyanhydride is prepared as described above, except that 1 mol of L-phenylalanine is used. Yield: 140 g (73%):

$^1$H-NMR (600 MHz, DMSO): δ=9.10 (s, 1H), 7.34-7.31 (m, 2H), 7.28-7.26 (m, 3H), 4.80 (t, J=6 Hz, 1H), 3.04 (d, J=6 Hz, 2H) ppm.

Example 3

Synthesis of

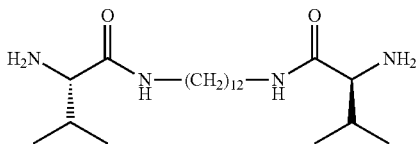

1,12-Dodecanediamine (5.0 g, 25 mmol) is dissolved in triethylamine (5.6 g, 55 mmol) and acetone (100 mL) and the solution is cooled to 10° C. In a second reactor, L-valine-N-carboxyanhydride (10.1 g, 77 mmol, see example 1) is dissolved in acetone (100 mL) and cooled to 10° C. The NCA-solution is added to the diamine solution at 10° C. and the reaction mixture is stirred 1.5 h at this temperature. The mixture is filtered through a pad of celite and the filtrate is concentrated at 20° C. The residue is treated with water (30 mL) and the pH is adjusted to 1-2 by addition of conc. HCl solution. The solution is concentrated and the residue is dissolved in isopropyl acetate (80 mL) and water (20 mL). The pH value is adjusted to 11 by addition of a NaOH solution. The organic phase is separated, washed with water (20 mL) and stirred at 0° C. for 1 h. The precipitate is filtered off, washed with cold isopropyl acetate (10 mL) and dried at 60° C. in vacuum. Yield: 6.28 g (63%).

$^1$H-NMR (600 MHz, DMSO): δ=7.75 (t, J=6 Hz, 2H), 3.10-2.99 (m, 4H), 2.88 (d, J=6 Hz, 2H), 1.85-1.80 (m, 2H), 1.58 (brs, 4H), 1.38 (t, J=6 Hz, 4H), 1.23 (s, 16H), 0.85 (d, J=6 Hz, 6H), 0.78 (d, J=6 Hz, 6H) ppm.

Example 4

Synthesis of

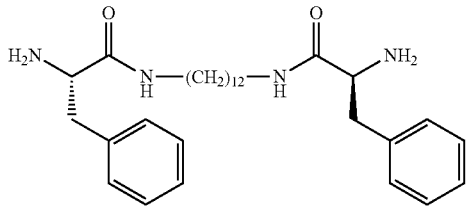

The same procedure as in example 3 is used except L-phenylalanine carboxyanhydride (77 mmol, example 2) is used as the starting reagent.

$^1$H-NMR (600 MHz, DMSO): δ=8.51 (t, J=6 Hz, 2H), 8.40 (brs, 4H), 7.32-7.24 (m, 10H), 4.00-3.97 (m, 2H), 3.12-3.01 (m, 6H), 2.93-2.87 (m, 2H), 1.36-1.17 (m, 20H) ppm.

Example 5

Synthesis of

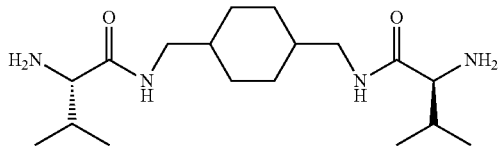 [SMILES: CC(C)[C@H](N)C(=O)NCC1CCC(CNC(=O)[C@@H](N)C(C)C)CC1]

The same procedure as in example 3 is used except that 1,4-Cyclohexanedimethaneamine is used as diamine.

$^1$H-NMR (600 MHz, DMSO): δ=7.65 (t, J=6 Hz, 2H), 3.21-3.11 (m, 4H), 2.77 (d, J=6 Hz, 2H), 2.10-2.04 (m, 2H) 1.95-1.90 (m, 2H), 1.62 (brs, 4H), 1.51-1.42 (m, 4H), 1.23-1.16 (m, 4H) 0.89 (d, J=6 Hz, 6H), 0.79 (d, J=6 Hz, 6H) ppm.

The invention claimed is:

1. Method for the synthesis of a compound according to formula I

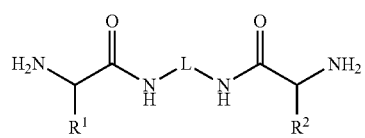

comprising the following steps:
a) reacting a N-carboxyanhydride according to formula II

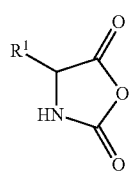

and a N-carboxyanhydride according to formula III

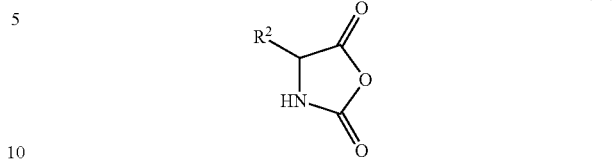

with a diamine according to formula IV

and
b) adding an acid to the reaction to adjust the pH value of the reaction to <7;
wherein
L represents a $C_2$-$C_{20}$ alkyl group, a $C_6$-$C_{20}$ aryl group, or a $C_7$-$C_{20}$ alkylaryl group; and
$R^1$ and $R^2$ can be identical or different and represent a hydrogen atom, a $C_1$-$C_4$ alkyl group, a $C_1$-$C_4$ hydroxyalkyl group, a $C_1$-$C_4$ thioether group, a $C_6$-$C_{20}$ aryl group, a $C_7$-$C_{20}$ alkylaryl group, a $C_7$-$C_{20}$ alkylhydroxyaryl group, or a $C_4$-$C_{20}$ alkylheteroaryl group with 1 to 4 heteroatoms;
or a $C_1$-$C_4$ alkylcarboxylic moiety, which may be an acid, an amide, or which may be esterified with a $C_1$-$C_6$ alkyl group or a $C_7$-$C_{20}$ alkylaryl group.

2. Method according to claim 1, wherein $R^1$ and $R^2$ can be identical or different and represent a hydrogen atom, a n-butyl group, a t-butyl group, a propyl group, a cyclopropyl group, an ethyl group, or one of the side chains of the amino acids alanine, valine, leucine, isoleucine, methionine, phenylalanine, tyrosine, tryptophan, serine, threonine, glutamine, asparagine, esters of glutamic acid, or esters of aspartic acid.

3. Method according to claim 1, wherein L represents a $C_6$-$C_{12}$ linear alkyl group, a 1,4-dimethylcyclohexyl group, or a xylene group.

4. Method according to claim 1, wherein in step b) the pH value is adjusted to 1 to 2.

5. Method according to claim 1, wherein mixing of the reactants in step a) is carried out at a temperature of −10 to +30° C.

6. Method according to claim 1, wherein in step a) the N-carboxyanhydrides according to formulae II and III are provided in an initial total molar amount that is 2 to 3.5-fold higher than the initial molar amount of the diamine.

7. Method according to claim 1, wherein the reaction in step a) is carried out in a polar aprotic solvent.

8. Method according to claim 7, wherein the solvent is selected from the group consisting of dichloromethane, methyl tert-butyl ether, tetrahydrofuran, ethyl acetate, isopropyl acetate, dimethylformamide, acetonitrile, dimethylsulfoxide, methyl isobutyl ketone, methyl ethyl ketone, acetone or mixtures thereof.

9. Method according to claim 2, wherein L represents a $C_6$-$C_{12}$ linear alkyl group, a 1,4-dimethylcyclohexyl group, or a xylene group.

10. Method according to claim 2, wherein in step b) the pH value is adjusted to 1 to 2.

11. Method according to claim 3, wherein in step b) the pH value is adjusted to 1 to 2.

12. Method according to claim 2, wherein mixing of the reactants in step a) is carried out at a temperature of −10 to +30° C.

13. Method according to claim 3, wherein mixing of the reactants in step a) is carried out at a temperature of −10 to +30° C.

14. Method according to claim 4, wherein mixing of the reactants in step a) is carried out at a temperature of −10 to +30° C.

15. Method according to claim 2, wherein in step a) the N-carboxyanhydrides according to formulae II and III are provided in an initial total molar amount that is 2 to 3.5-fold higher than the initial molar amount of the diamine.

16. Method according to claim 3, wherein in step a) the N-carboxyanhydrides according to formulae II and III are provided in an initial total molar amount that is 2 to 3.5-fold higher than the initial molar amount of the diamine.

17. Method according to claim 4, wherein in step a) the N-carboxyanhydrides according to formulae II and III are provided in an initial total molar amount that is 2 to 3.5-fold higher than the initial molar amount of the diamine.

18. Method according to claim 5, wherein in step a) the N-carboxyanhydrides according to formulae II and III are provided in an initial total molar amount that is 2 to 3.5-fold higher than the initial molar amount of the diamine.

19. Method according to claim 2, wherein the reaction in step a) is carried out in a polar aprotic solvent.

20. Method according to claim 3, wherein the reaction in step a) is carried out in a polar aprotic solvent.

\* \* \* \* \*